(12) United States Patent
Murakami

(10) Patent No.: US 6,648,876 B2
(45) Date of Patent: Nov. 18, 2003

(54) LASER TREATMENT APPARATUS

(75) Inventor: Naho Murakami, Hoi-gun (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 09/994,817

(22) Filed: Nov. 28, 2001

(65) Prior Publication Data

US 2002/0068925 A1 Jun. 6, 2002

(30) Foreign Application Priority Data

Dec. 4, 2000 (JP) ......................... 2000-372935

(51) Int. Cl.$^7$ ................................. A61F 9/008
(52) U.S. Cl. ................................. 606/4; 606/6
(58) Field of Search .................. 606/4–6; 353/69

(56) References Cited

U.S. PATENT DOCUMENTS

| | | | |
|---|---|---|---|
| 3,670,260 A | * | 6/1972 | Koester et al. ............ 372/9 |
| 4,838,266 A | | 6/1989 | Koziol et al. |
| 4,880,299 A | | 11/1989 | Hamada |
| 5,171,242 A | | 12/1992 | Dewey et al. |
| 5,263,951 A | | 11/1993 | Spears et al. |
| 5,336,216 A | | 8/1994 | Dewey |
| 5,505,723 A | | 4/1996 | Muller |
| 6,354,707 B1 | * | 3/2002 | Jeon et al. ............ 353/69 |

FOREIGN PATENT DOCUMENTS

| | | |
|---|---|---|
| EP | 1 074 232 A1 | 2/2001 |
| JP | A 6-254112 | 9/1994 |
| WO | WO 98/41178 | 9/1998 |

\* cited by examiner

*Primary Examiner*—Lee Cohen
*Assistant Examiner*—Henry M. Johnson, III
(74) *Attorney, Agent, or Firm*—Oliff & Berridge, PLC

(57) ABSTRACT

A laser treatment apparatus provided with a light delivery optical system for delivering a laser beam for treatment from a laser source to a treatment area of a patient's eye to irradiate the treatment area is disclosed. The light delivery optical system includes a homogenizer optical system which substantially uniformizes an energy distribution of the laser beam; a relay optical system having lenses for relaying an image of an exit end face of the homogenizer optical system onto the treatment area; and a distortion generating optical system which is disposed between the homogenizer optical system and the relay optical system and generates a negative distortion in the exit end face image to be formed on the treatment area.

9 Claims, 5 Drawing Sheets

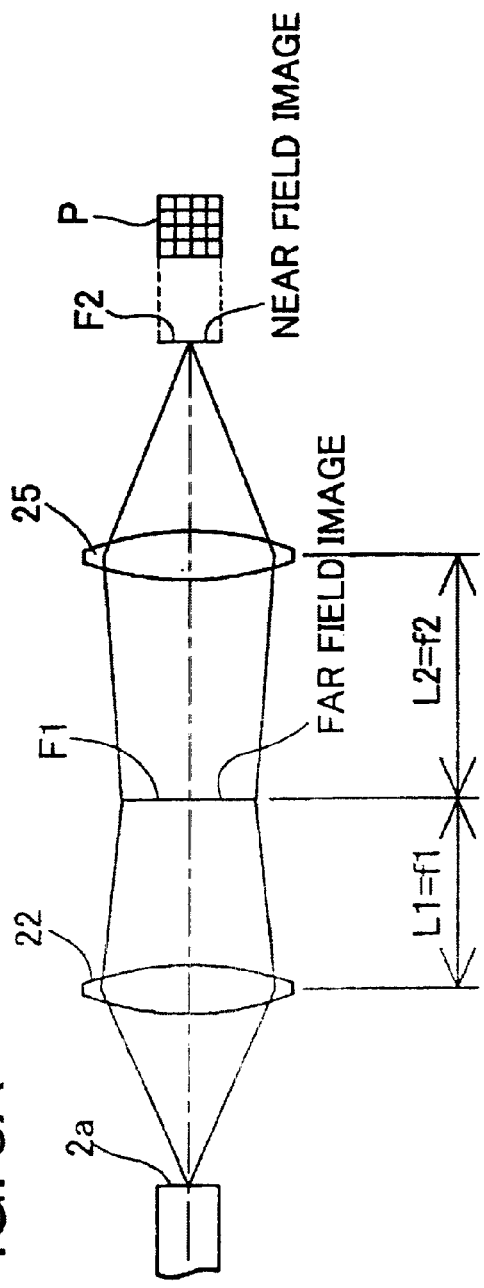
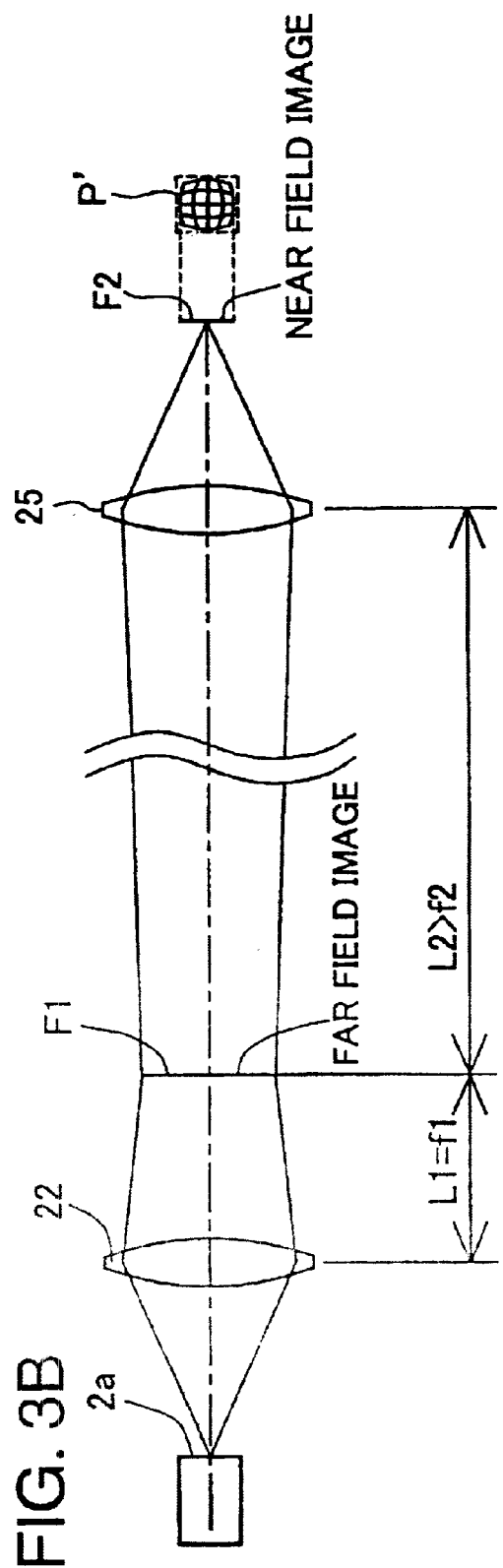

LASER TREATMENT APPARATUS

BACKGROUND OF THE INVENTION

1. Field of the Invention

The present invention relates to a laser treatment apparatus for performing photocoagulation treatment by irradiating a part to be treated, i.e., an affected part, with a laser beam for treatment.

2. Description of Related Art

As laser treatment apparatus for photocoagulation by laser irradiation, there are an apparatus of a defocusing type which performs the laser irradiation by delivering a laser beam for treatment from a laser source to a part to be treated (a treatment area) through an optical fiber without focusing an image of an exit end face of the optical fiber on the treatment area and another apparatus of a parfocal type which performs the laser irradiation while focusing the exit end face image on the treatment area. In the apparatus of the parfocal type, it an energy distribution (intensity distribution) of the laser beam is uniform at the exit end face of the optical fiber, the energy distribution on the irradiation part of the treatment area also becomes uniform. Therefore, this parfocal type apparatus is considered more preferable than the defocusing type apparatus which performs the laser irradiation with the energy distribution of the laser beam being higher on the center portion of the irradiation part than the peripheral portion.

With the use of the parfocal type apparatus, the energy distribution on the irradiation part becomes uniform, whereas the tissue of the irradiation part does not react uniformly. This may bring about a tendency to concentrate heat on the center portion, which first begins to be burned. As a result, a uniform coagulation spot could not be obtained. In particular, this remarkably appears when the spot size of the laser beam is set to be large.

SUMMARY OF THE INVENTION

The present invention has been made in view of the above circumstances and has an object to overcome the above problems and to provide a laser treatment apparatus capable of producing a more uniformly coagulated state (coagulation spot) of a laser irradiation part of a treatment area.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus provided with a light delivery optical system for delivering a laser beam for treatment from a laser source to a treatment area of a patient's eye to irradiate the treatment area, the light delivery optical system including: a homogenizer optical system which substantially uniformizes an energy distribution of the laser beam; a relay optical system having lenses for relaying an image of an exit end face of the homogenizer optical system onto the treatment area; and a distortion generating optical system which is disposed between the homogenizer optical system and the relay optical system and generates a negative distortion in the exit end face image to be formed on the treatment area.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIGS. 3A and 3B are views each showing an optical arrangement for generating a negative distortion;

DETAILED DESCRIPTION OF THE PREFERRED EMBODIMENTS

Figure 1:
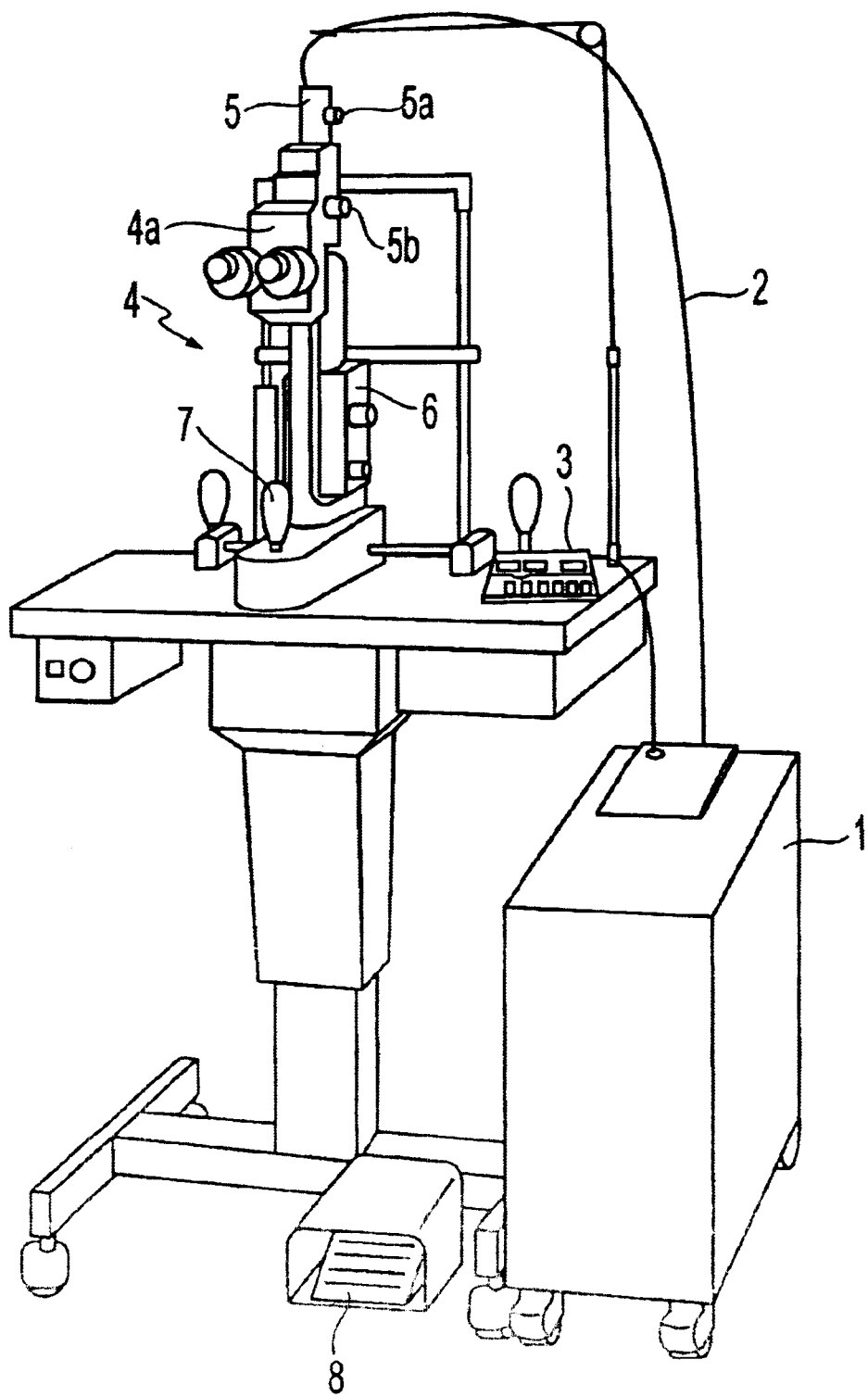
FIG. 1 is a perspective view of a laser treatment apparatus used in an embodiment according to the present invention.
Figure 2:
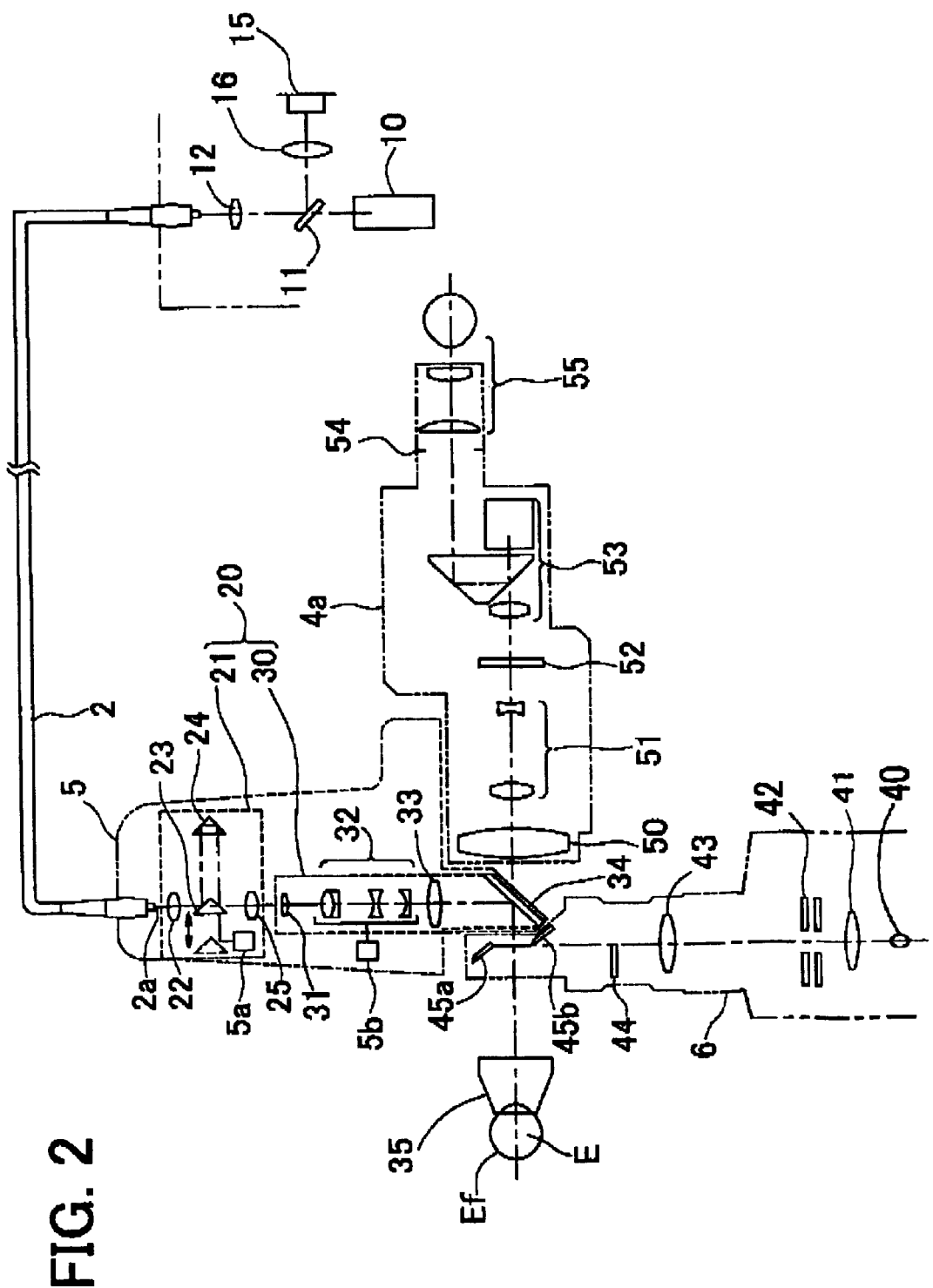
FIG. 2 is a schematic structural view of an optical system of the apparatus.

A detailed description of a preferred embodiment of a laser treatment apparatus embodying the present invention will now be given referring to the accompanying drawings. FIG. 1 is a perspective view of the laser treatment apparatus for photocoagulation with respect to a patient's eye, for example, the fundus of the eye. FIG. 2 is a schematic structural view of an optical system of the apparatus.

Numeral 1 is a main unit of the apparatus, which is internally provided with a laser source 10 which emits a laser beam for treatment, a light source 15 which emits an aiming beam, an optical system for making the aiming beam and the laser beam for treatment (hereinafter simply referred to as a laser beam) incident on an optical fiber 2.

Numeral 3 is a control part for making settings of laser irradiation conditions such as power of the laser beam, irradiation time, and other settings necessary for the apparatus. Numeral 4 is a slit-lamp delivery for irradiating the laser beam to a treatment area of a patient's eye E while allowing an operator to observe the eye E. This slit-lamp delivery 4 are constructed of an irradiation part 5 for emitting the laser beam delivered thereto through the fiber 2, an illumination part 6 for slit-illuminating the patient's eye E, and a binocular microscopic part 4a. Numeral 8 is a footswitch for generating a trigger signal to start laser irradiation.

The irradiation part 5 is provided with an insertion/removal knob 5a which is operated for inserting or removing a first prism 23 (see FIG. 2) disposed in the irradiation part S into or from the optical path of the laser beam and a spot size adjusting knob 5b which is operated for changing a diameter (spot size) of a spot image of the laser beam to be formed on the treatment area, i.e., an image of an exit end face 2a of the fiber 2. By operation of the knob 5b, the spot size of the laser beam can be changed in a range of 50 to 500 μm in diameter.

The laser beam from the laser source 10 is condensed on an incident end face of the fiber 2 through a condenser lens 12, thus entering the fiber 2. A dichroic mirror 11 is disposed between the lens 12 and the laser source 10. The aiming beam, which is visible, emitted from the light source 15 passes through a collimator lens 16, is deflected by the dichroic mirror 11, and then made coaxial with the laser beam. It is to be noted that, as the laser source 10 in the present embodiment, an Nd:YAG laser which oscillates a fundamental wave of 1064 nm is used to produce green light with a wavelength of 532 nm (linearly polarized light), which is double the fundamental wave. The light source is a laser diode which emits red light with a wavelength of 630 nm.

The laser beam is delivered to the irradiation part S through the fiber 2. With the use of this fiber 2, the energy distribution of the laser beam to be emitted from the exit end face 2a of the fiber 2 is substantially uniformized. The irradiation part 5 is internally provided with an irradiation optical system 20 for delivering the laser beam emitted from the fiber 2 onto the treatment area. The irradiation optical system 20 includes a distortion generating optical system 21 for generating a negative distortion in a near-field image of the laser beam emitted from the exit end face 2a of the fiber 2 at an image forming position of the near-field image and a relay optical system 30 for delivering the laser beam from the distortion generating optical system 21 or the fiber 2 to a treatment area.

The distortion generating optical system 21 is structured of a first short-focal-length lens 22, a first prism 23, a second prism 24, and a second short-focal-length lens 25. The first prism 23 is arranged to be movable in a direction indicated by an arrow in FIG. 2 by means of a rack and pinion mechanism provided in the irradiation part 5. Thus, the first prism 23 can be inserted into or removed from the optical path of the laser beam with the turn of the knob 5a by a predetermined amount. When the first prism 23 is placed in the optical path, the laser beam emitted from the exit end face 2a of the fiber 2, which is a circular end face, passes through the first short-focal-length lens 22 and is deflected by the first prism 23. The laser beam is then turned back by the second prism 24 toward the first prism 23. The laser beam is deflected again by the first prism 23 to pass through the second short-focal-length lens 25.

In the present embodiment, the use of the first and second prisms 23 and 24 can ensure an appropriate length of the optical path from the first short-focal-length lens 22 to the second short-focal-length lens 25 in a saved space. Naturally, the present invention is not limited to the above arrangement and, instead thereof, may use a plurality of reflection mirrors or the like to provide a necessary optical path length.

The relay optical system 30 consists of a relay lens 31, a group of zoom lenses 32, an objective lens 33, and a movable mirror 34 for changing an emission direction of the laser beam. The zoom lens group 32 is moved in a direction of the optical axis by operation of the knob 5b to change a magnification of an image of the laser beam to be formed on the treatment area The irradiation of the laser beam to the treatment area of an eye fundus ES of the patient's eye E is performed through a contact lens 35 put on the eye E.

The illumination part 6 includes an illumination light source 40. Illumination light from this light source 40 passes through a condenser lens 41, slit plates 42, and a projection lens 43, and the illumination light is then reflected by splitting mirrors 45a and 45b to illuminate the patient's eye E. Numeral 44 is a correcting lens for correcting the length of an optical path of the illumination light reflected by the splitting mirror. The binocular microscopic part 4a includes an objective lens 50, a magnification varying optical system 51, a protective filter 52, a group of erect prisms 53, a field diaphragm 54, and eyepiece lenses 55.

Next, generation of a negative distortion by means of the distortion generating optical system 21 is explained with reference to FIGS. 3A and 3B. In FIGS. 3A and 3B, for the sake of convenience in explanation, the prisms 23 and 24 are unillustrated, but shown by a straight line, and the exit end face 2a of the fiber 2 is shown in a rectangular form.

As shown in FIGS. 3A and 3B, an image forming position of a far-field image of the laser beam emitted from the exit end face 2a (an image forming position of a fiber far-field image), namely, a light condensing position of the laser beam passed through the first lens 22 from an infinite distance, corresponds to a position F1 at a focal length f1 of the first lens 22. An image forming position of a near-field image of the laser beam emitted from the exit end face 2a (an image forming position of a fiber near-field image) corresponds to an image forming position F2 of the second lens 25. In the present embodiment, the distance from the first lens 22 to the position F1 is designated as L1, and the distance from the position F1 to the second lens 25 is designated as L2.

When the distance from the lens 22 to the lens 25 is short as shown in FIG. 3A and equal to the sum of the focal length f1 of the lens 22 and the focal length f2 of the lens 25 (i.e., L1+L2=f1+f2), no negative distortion occurs in an image formed at the position F2, so that the image is of a shape P corresponding to the shape of the exit end face 2a.

As shown in FIG. 3B, on the other hand, when the distance L2 between the position F1 and the lens 25 is set longer than the length f2 (i.e., L1+L2>f1+f2), a negative distortion occurs in the image formed at the position F2, so that the image is of, for example, a shape P'.

Basically, distortion is a defect which entirely distorts the shape of an image. In the case of a negative distortion, a real image height becomes smaller than an ideal image height. Therefore, a near-field image at the position F2 where the negative distortion occurs has an energy distribution with a center part lower than a peripheral part, namely, a concave form. In the present invention, this characteristic of distortion is utilized to form the near-field image with the negative distortion on the treatment area. With this arrangement, the concentration of heat on the center portion can be reduced, which can provide uniform coagulation effect on the entire area of the irradiation part by the laser beam.

It is to be noted that the distance L2 from the position F1 to the lens 25 is determined according to a rate of generation of the negative distortion in order to produce a uniform coagulation effect on the irradiation part. In the present embodiment, the length of the optical path is sufficiently extended with the use of the first and second prisms 23 and 24 so that the negative distortion occurs at a rate of about 10% on the irradiation part when the focal lengths of the lens 22 and the lens 25 are made equal and the spot size is set at 500 $\mu$m in diameter. When the negative distortion is generated, a peripheral portion of the image may appear blurred on the irradiation part. As mentioned above, however, the generation rate of the negative distortion is controlled to be about 10%, so that a coagulation spot can be produced in a substantial spot size as set.

Next, operation of the apparatus provided with the above structure is explained below.

An operator first observes the eye fundus Ef through the microscopic part 4a, the eye fundus Ef being illuminated by illumination light from the illumination part 6. While observing the aiming beam irradiated to the eye fundus Ef, the operator manipulates the knob 5b to set a desired spot size. At this time, if a relatively large spot size (in a range of 200 to 500 $\mu$m in diameter) is set for photocoagulation, the first prism 23 needs to be held as inserted in the optical path. In order to determine the laser irradiation conditions, the operator sets irradiation time, power, irradiation time interval, and others with various switches on the control part 3. These setting conditions are determined based on operator's experience according to a condition of the affected part and others.

Subsequently, the operator operates a joystick 7 and an unillustrated manipulator to make alignment of the aiming beam with respect to the treatment area. The operator adjusts the aiming beam to an image forming position of the near-field image so that the size of the aiming beam becomes the minimum on the treatment area of the eye fundus Ef, in other words, so that the aiming beam becomes parfocal with the near-field image. The operator then presses the footswitch 8 to start laser irradiation. The laser beam from the laser source 10 is delivered to the irradiation part 5 through the fiber 2 and then the distortion generating optical system 21 produces an image with a negative distortion on the irradiation part.

Figure 4A:
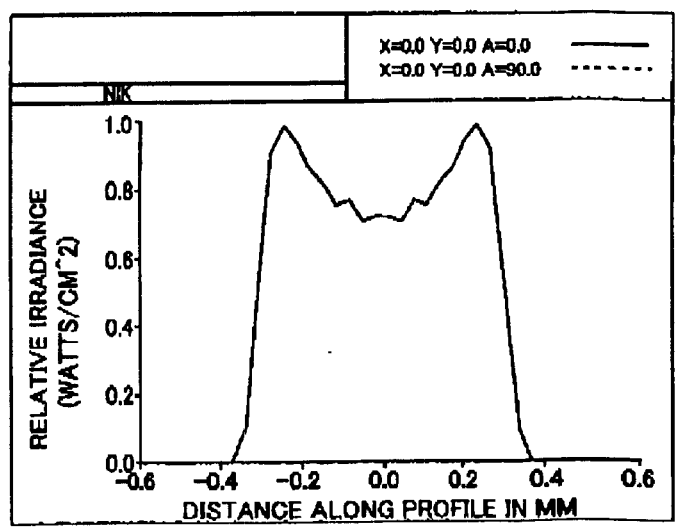
FIGS. 4A, 4B, and 4C are graphs each showing an energy distribution of a laser beam on an irradiation part.

FIG. 4A is a graph showing a calculated energy distribution of the laser beam on the irradiation part in the case where the negative distortion is generated by the first prism 23 disposed in the optical path. In the present embodiment, the distance of the optical path between the lens 22 to the lens 25 is set at 200 mm and the spot size of the laser beam is set at 500 μm in diameter. In the graph, the horizontal axis indicates the size of a spot and the vertical axis indicates the energy intensity.

As shown in the graph, when the laser irradiation is effected so that the negative distortion is generated, the energy intensity in the center portion of the irradiation part is low while that in the peripheral portion is high. In the photocoagulation by laser irradiation onto the eye fundus Ef, therefore, heat can not concentrate on the center portion, suppressing the tendency to begin to burn the irradiation part from the center portion. This makes it possible to easily form a coagulated part in a uniformly burned state.

On the other hand, in the laser irradiation using the laser beam with a substantially uniform energy distribution on the irradiation part as conventional, the knob 5a is operated to remove the first prism 23 from the optical path, setting the optical path length from the lens 22 to the lens 25 to be an optical path length which causes no negative distortion to occur, and the laser beam is thus irradiated. For example, in the case of treatment for glaucoma, which is performed by perforating the iris or the like of a patient's eye with the use of a laser beam of a small spot size, the laser irradiation is effected with the energy distribution made substantially uniform as conventional.

Figure 4B:
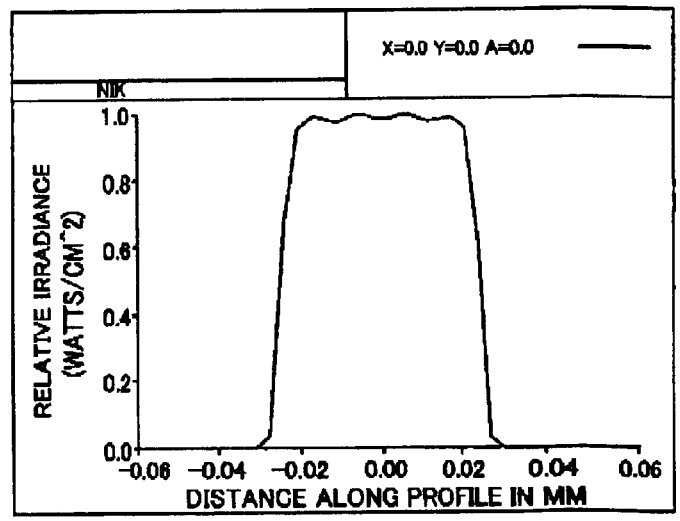

FIG. 4B is a graph showing the energy distribution of the laser beam on the irradiation part in the case where the first prism 23 is removed from the optical path. In this case, the spot size is set at 50 μm in diameter. As shown in this graph, the energy distribution becomes uniform and therefore the laser beam can be uniformly condensed to efficiently perforate the iris.

Figure 4C:
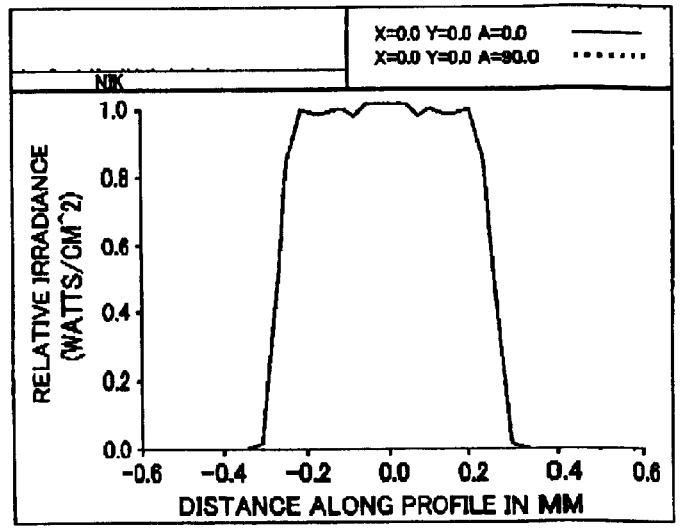

In the case of a large spot size (500 μm in diameter in the present embodiment), the knob 5a is operated to remove the first prism 23 from the optical path. As a result, the laser beam with a uniform energy distribution on the irradiation part can be obtained as shown in FIG. 4C.

In the present embodiment, the apparatus is arranged so that a negative distortion occurs when the spot size is in a range of 200 to 500 μm in diameter, while no negative distortion occurs when the spot size is less than 200 μm in diameter. The present invention is not limited to the above embodiment. For example, the apparatus may be constructed to generate a negative distortion even when the spot size is less than 200 μm in diameter. Furthermore, a forming state of the negative distortion may be changed according to the spot size.

Figure 5:
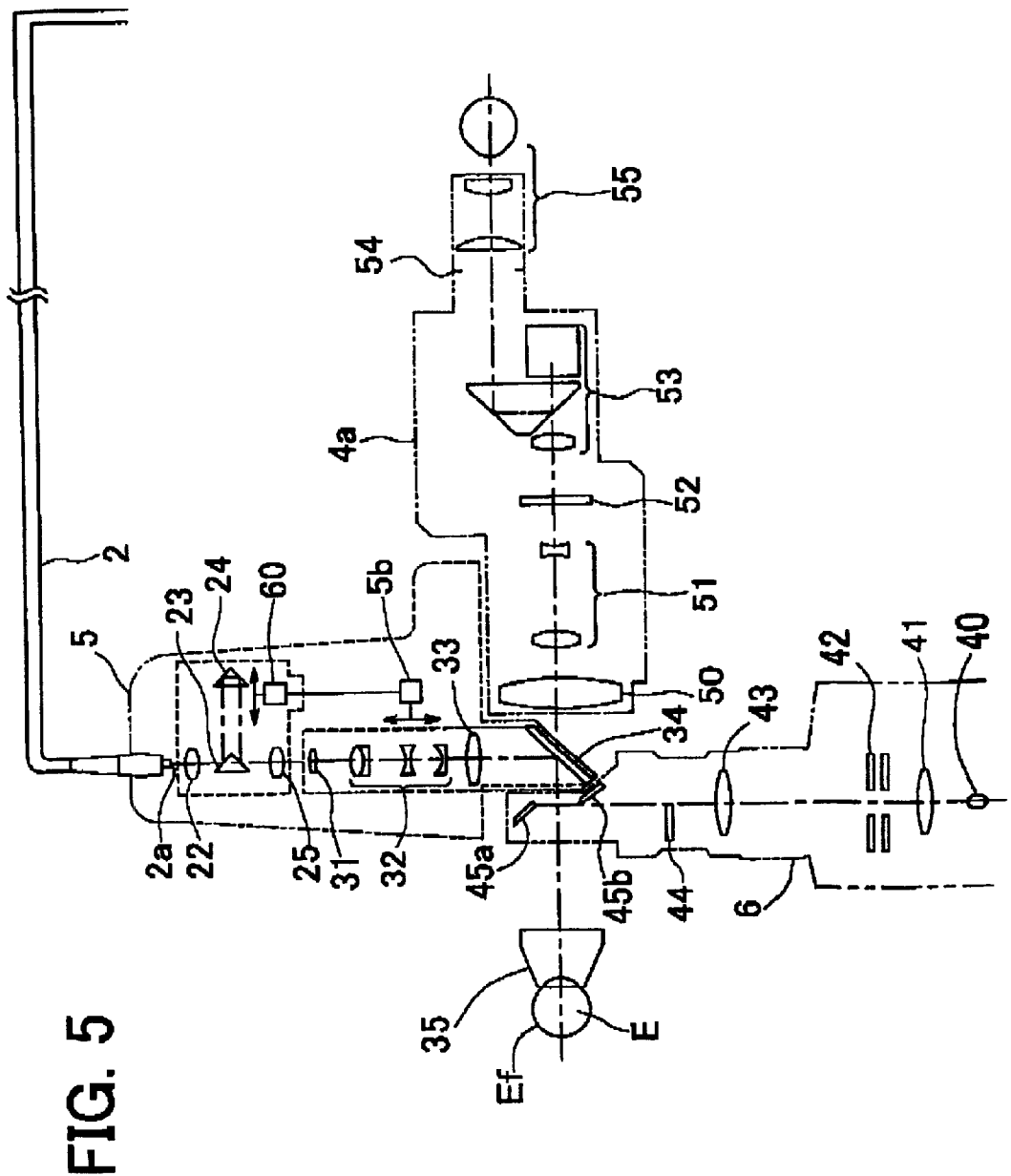
FIG. 5 is a view of an optical system for changing a forming state of the negative distortion to a spot size of the laser beam.

FIG. 5 is a schematic view of an optical system for changing the forming state of the negative distortion according to the spot size. Elements with like numerals corresponding to those in the above embodiment have like functions.

As shown in FIG. 5, when the spot size of the laser beam to be formed by the zoom lens group 32 changed by operation of the knob 5b, the second prism 24 is moved in a direction indicated by an arrow according to the change amount of the zoom lens group-32. For example, an operation signal from the knob 5b is input to a moving mechanism 60 constructed of a motor and others, and the moving mechanism 60 moves the second prism 24 in response to the operation signal. The moving position of the second prism 24 is determined in advance in accordance with the spot size to be set. It is to be noted that the movement of the second prism 24 may be mechanically performed by a rack and pinion mechanism which is operated with the knob 5b.

With the above structure, operating the knob 5b causes the spot size of the laser beam to change, thereby moving the second prism 24 in accordance with the change amount of the spot size. Thus, the optical path length from the lens 22 to the lens 25 is changed. As a result thereof, a near-field image with a negative distortion corresponding to the spot size can be formed.

This formation of the near field image having the negative distortion in accordance with the spot size allows more preferable photocoagulation.

The present invention may be embodied in other specific forms without departing from the essential characteristics thereof. For instance, the fiber 2 is used to deliver from the laser source 10 to the irradiation optical system 20 in the above embodiment. Instead of this fiber 2, a homogenizer optical system may be inserted between the laser source 10 and the irradiation optical system 20. This optical system can provide the same effect as above.

The laser source 10 used in the above embodiment is an Nd:YAG laser, but it is not limited thereto. Any lasers usable in photocoagulation treatment on an eye fundus, for example, a krypton laser, a laser diode, or the like, may be applied.

According to the present invention, as explained above, the energy distribution of the laser beam on the irradiation part can be controlled to be lower in a center part than a peripheral part (in a concave state). Consequently, the tendency to begin to burn the irradiation part from the center portion can be suppressed, thus forming a good coagulated state.

The foregoing description of the preferred embodiment of the invention has been presented for purposes of illustration and description. It is not intended to be exhaustive or to limit the invention to the precise form disclosed, and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A laser treatment apparatus provided with a light delivery optical system for delivering a laser beam for treatment from a laser source to a treatment area of a patient's eye to irradiate the treatment area, the light delivery optical system including:

an optical fiber for delivering the laser beam from the laser source;

a distortion generating optical system which forms an image of an exit end face of the optical fiber and generates a negative distortion in the exit end face image to be formed on the treatment area; and a relay optical system which forms an image of the exit end face formed by the distortion generating optical system on the treatment area.

2. The laser treatment apparatus according to claim 1, wherein the distortion generating optical system includes a first lens disposed on an exit end face side and a second lens disposed on a relay optical system side, a focal length of the first lens is shorter than a focal length of the second lens.

3. The laser treatment apparatus according to claim 2, wherein the distance from the first lens to the second lens is determined so that a generation rate of the negative distortion is a predetermined value.

4. The laser treatment apparatus according to claim 2, wherein the distortion generating optical system is provided with an optical system which changes a length of an optical path from the first lens to the second lens, the optical system being disposed between the first and second lenses.

5. The laser treatment apparatus according to claim 4, wherein the optical path length changing optical system is provided with a first reflection member removably disposed in the optical path between the first and second lenses.

6. The laser treatment apparatus according to claim 5, wherein the optical path length changing optical system is provided with a second reflection member which is movably disposed and reflects the laser beam reflected by the first reflection member.

7. The laser treatment apparatus according to claim 4, wherein the optical path length changing optical system is provided with a first reflection member disposed in the optical path between the first and second lenses and a second reflection member which is movably disposed and reflects the laser beam reflected by the first reflection member.

8. The laser treatment apparatus according to claim 4, wherein the relay optical system is provided with a magnification varying optical system which changes an image-forming magnification of the exit end face image on the treatment area, and the optical path length changing optical system changes the length of the optical path in accordance with a change in the image-forming magnification by the magnification varying optical system.

9. The laser treatment apparatus according to claim 1, wherein the distortion generating optical system forms the energy distribution of the laser beam into a substantially concave state on the treatment area.

* * * * *